United States Patent [19]
Cardinal et al.

[11] 4,319,194
[45] Mar. 9, 1982

[54] METHOD OF AND APPARATUS FOR MONITORING PLATELET AGGREGATION AND TEST CELL FOR USE IN SUCH METHOD AND APPARATUS

[75] Inventors: David C. Cardinal, Tonbridge; Roderick J. Flower, Biggin Hill, both of England

[73] Assignees: Burroughs Wellcome Co., Triangle Park, N.C.; Wellcome Foundation Ltd., London, England

[21] Appl. No.: 80,525

[22] Filed: Oct. 1, 1979

[30] Foreign Application Priority Data

Oct. 2, 1978 [GB] United Kingdom ............... 39006/78

[51] Int. Cl.³ ............................................ G01N 27/02
[52] U.S. Cl. .................. 324/449; 23/230 B; 73/61.1 R; 128/637
[58] Field of Search ....................... 324/449, 442, 65 P; 73/61 R, 61.1 R; 128/637, 669; 23/230 B

[56] References Cited

U.S. PATENT DOCUMENTS

| | | |
|---|---|---|
| 2,555,937 | 6/1951 | Rosenthal et al. ............... 324/442 X |
| 2,651,751 | 9/1953 | Heath . |
| 2,769,141 | 10/1956 | Richardson ........................ 324/442 |
| 3,250,987 | 5/1966 | Okada et al. .................... 324/442 X |
| 3,267,362 | 8/1966 | Page ............................. 23/230 B X |
| 3,267,364 | 8/1966 | Page et al. ..................... 23/230 B X |
| 3,524,727 | 8/1970 | Noller . |
| 3,555,937 | 1/1971 | Nicodemas . |
| 3,648,159 | 3/1972 | Stansell et al. ................. 73/61 R X |
| 3,699,437 | 10/1972 | Ur . |
| 3,840,806 | 10/1974 | Stoner et al. . |
| 3,861,877 | 1/1975 | Matharani et al. ............. 73/61 R X |
| 3,900,290 | 8/1975 | Hornstra ......................... 73/61 R X |
| 4,082,085 | 4/1978 | Wardlaw et al. ............. 73/61.1 R X |
| 4,116,564 | 9/1978 | Renaud et al. . |

FOREIGN PATENT DOCUMENTS 1022822 1/1958 Fed. Rep. of Germany .
1526852 10/1978 United Kingdom .

OTHER PUBLICATIONS

Bicher, H.I., "The 'Membrane Capacitance' Aggregometer-A Method for Measuring Platelet Aggregation in Whole Blood", Angiology 22 (5): 285-294, May 1971.

*Primary Examiner*—Stanley T. Krawczewicz
*Attorney, Agent, or Firm*—Lewis H. Eslinger

[57] ABSTRACT

Aggregation of blood-platelets is detected by using a test cell which contains two electrodes which extend into the sample. So as to maximize the change in resistance between the electrodes which occurs as platelets aggregate on them, they are each rod-shaped and of not more than about 0.25 mm in diameter. The resistance between the electrodes is detected using an AC signal to avoid polarization effects.

The test cell may be constructed so as to be a disposable item.

10 Claims, 7 Drawing Figures

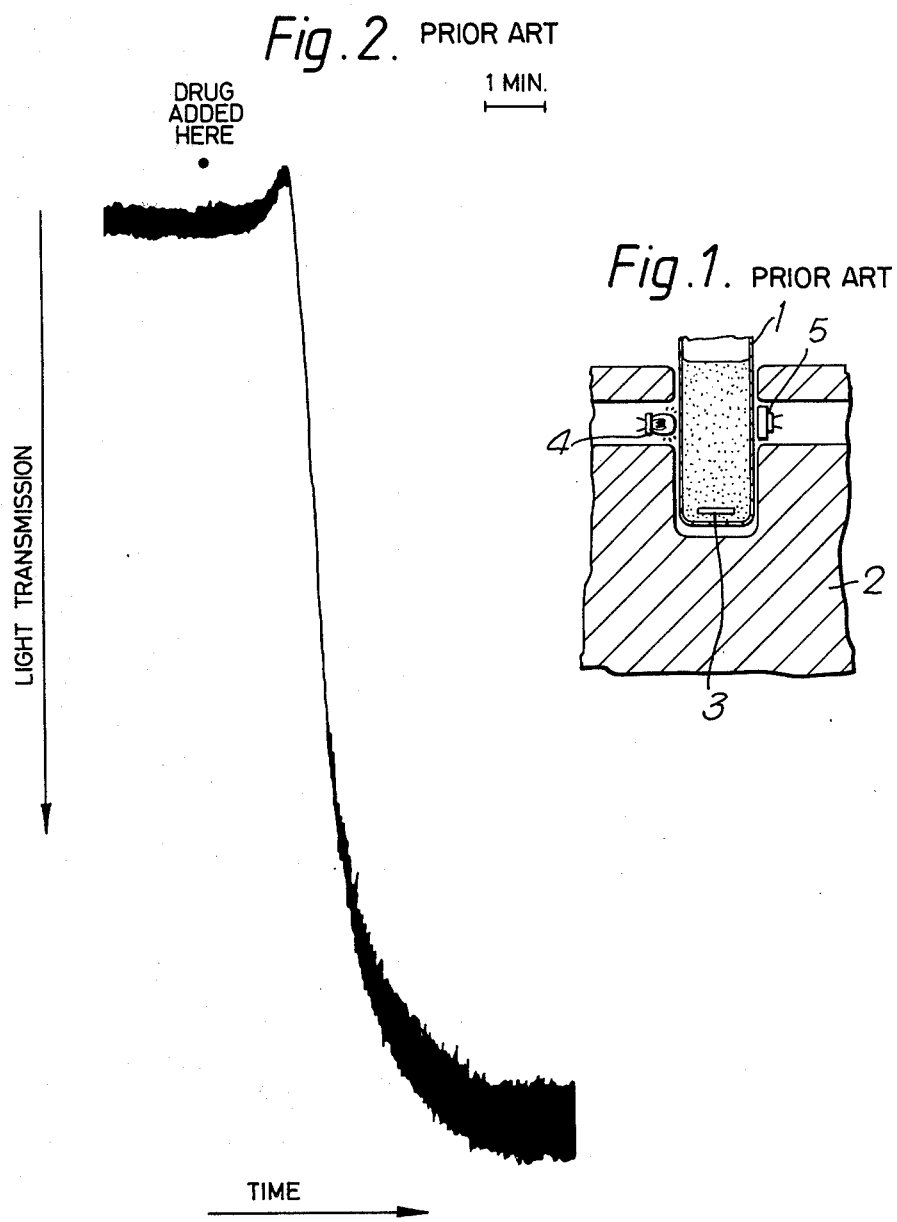

METHOD OF AND APPARATUS FOR MONITORING PLATELET AGGREGATION AND TEST CELL FOR USE IN SUCH METHOD AND APPARATUS

DESCRIPTION

The present invention relates to a method of, and apparatus for monitoring blood platelet aggregation and to a test cell for use in such a method and apparatus.

"Blood" consists of cells suspended in a protein rich fluid called plasma. There are three major groups of cells in blood: The most numerous are the "red cells" (in man, about $5.5 \times 10^6/mm^3$) which specialise in oxygen transport. The "white cells" (about $7000/mm^3$) are involved one way or the other in combating infection. The third group are the platelets ($250,000/mm^3$)—these are small disc-shaped cells and their chief function is to maintain the integrity of the vascular system—not only during injury, but also day-to-day wear and tear. To do this, platelets can, when they come into contact with certain materials and chemicals (especially those released from damaged cells), undergo a process known as the aggregation-adhesion reaction. When they aggregate platelets change from their discoid shape to a more spherical form, they throw out long processes known as pseudopodia and somehow become "sticky". The result of this is that they stick to one another and to the damaged tissue, thus plugging gaps or holes in the blood vessel wall. Although their primary response is to aggregate a secondary "release reaction" may also occur, during which platelets release materials which accelerate the clotting process.

The phenomenon of aggregation is the most widely studied property of platelets: it is of interest not only for scientific reasons (platelets make an ideal test system for examining cellular mechanisms and drug action), but also has diagnostic significance since there are many conditions in which platelet function is abnormal, and screening of platelet function is in fact a common haematological test.

The method most often used for measuring the platelet aggregation-adhesion reaction is the "Born aggregometer", first described in 1962. The principle of the method is quite simple: After the addition of a suitable anti-coagulant a blood sample is gently centrifuged. This separates the blood into two fractions; the red and white cells which are heavy settle at the bottom of the tube leaving the straw coloured plasma containing the platelets at the top of the tube. This top layer is carefully removed and is generally referred to as "platelet rich plasma" (PRP for short). In order to measure the aggregation response small aliquots of PRP are transferred to a small glass cuvette, referenced 1 in FIG. 1 of the accompanying drawings, which is maintained at body temperature (37° C.) by being positioned in a heated block 2 and constantly stirred (at a known speed) by a bar 3 to facilitate mixing. A narrow light beam from a light source 4 shines through the glass cuvette containing the PRP and the transmitted light is measured the other side of the cuvette by means of sensitive photocell 5. In untreated PRP the majority of the light is scattered by the platelets and transmission is minimal; when an aggregating agent is added to the cuvette the platelets clump together and the light transmission increases. This event is generally displayed on a chart recorder so that a permanent record is obtained, such a trace is seen in FIG. 2. In this case the aggregating agent is collagen (a type of connective tissue found in blood vessels and many other places in the body) and notable features of the aggregation include a delay time and an irreversible aggregation. Not all aggregating agents are irreversible, and some may induce aggregation immediately with no delay time.

One serious drawback of the Born aggregometer is the necessity to first separate the blood by centrifugation and remove the PRP. This process characteristically takes 20-25 min and is disadvantageous for two reasons: Firstly, it is obviously rather unphysiological to study platelet function in PRP since it is quite likely that red or white cells influence platelet function in vivo. Secondly, many important mediators generated by platelets in vivo are very labile and may survive in blood for only a matter of minutes. It is therefore impossible to study the effect of these mediators on platelet function properly when it takes 20-25 min after the blood has been sampled to perform the aggregation test.

One of the difficulties with conventional optical aggregometers is because they rely on light transmission they cannot be used with whole blood. One previous proposal to overcome this difficulty is described in "The membrane capacitance aggregometer—a method for measuring platelet-aggregation in whole blood", H. I. Bicher, Angiology 22 (5): 285-94 May 1971. In that device, the change in capacitance between two electrodes resulting from platelet aggregation is measured. However, measurement of capacitance, or even change in capacitance in the capacitance range in question, namely about 10 to 100 femtofarads is notoriously difficult, such apparatus tends to be prone to drift and disturbance by outside influences.

The invention thus seeks to provide a method of and apparatus for monitoring platelet aggregation which avoids the disadvantages of the previous optical and membrane capacitance aggregometers.

Our solution thus relies upon a different principle for its operation from the prior aggregometers and because it does not require a light transmitting sample it can be utilized with whole blood as well as with PRP. Thus our apparatus relies upon the covering by platelets of foreign objects placed in the cuvette. In our apparatus these "foreign objects" are electrodes, e.g. two fine platinum wires. During the initial contact with the sample the electrodes become coated with a platelet monolayer. In the presence of aggregating agents, however further platelets then stick to the monolayer and progressively build up on the electrodes. This build-up of platelets can be quantized by measuring the increase in resistance between the platinum wires.

Thus, according to the present invention we provide a method of monitoring blood-platelet aggregation in a platelet-containing sample comprising the step of monitoring the change in electrical resistance between rod shaped electrodes in the sample while relative movement of the sample and electrodes occurs, the electrodes being not more than approximately 0.25 mm in diameter.

The invention also provides apparatus for monitoring blood-platelet aggregation comprising: a test cell for a platelet-containing sample; a plurality of electrodes and associated means for mounting them in predetermined positions with respect to one another in the test cell, the electrodes each being rod shaped and not more than approximately 0.25 mm in diameter; and circuitry for monitoring the change in electrical resistance between the electrodes.

The change in resistance between the electrodes which takes place during platelet aggregation appears not to result from e.g. changes in ion concentrations, but rather from the masking effect which the platelets have as they adhere to the electrodes thereby reducing the surface area of the electrodes which is in contact with the liquid. The shape and dimensions of the electrodes are of significance both from the point of view of their surface area, which should be minimised (since although the number of platelets in a sample may be very large, the area which they are capable of masking, and thus the attendant change in resistance, is quite small) and because platelets seem to "prefer" to adhere to fine wires. One electrode configuration which we found to be particularly advantageous consists of two parallel wires each of 0.25 mm diameter spaced apart by about 1 mm and each having about 1 cm of their length exposed to the liquid these being mounted on a removable lid of the test cell.

While the resistance monitoring is taking place, relative movement of the sample and electrodes needs to occur as this increases the likelihood of aggregating platelets coming into contact with the electrodes. This relative movement may be achieved by stirring in the case of a unit sample and is of course inherent when the test cell is adapted for a through-flow of blood. Where the sample is stirred, the electrodes are preferably mounted off-centre with respect to the test cell holding the sample since the centre is of course where the flow of liquid during stirring is at a minimum.

The separation between the electrodes has a significant effect on the operation of the apparatus. Test cells have been produced with an electrode separation of 2 mm and have worked satisfactorily; this separation is at the upper limit of values which would give satisfactory results.

The test cell may be produced as a disposable item to avoid the need for cleaning of a cell between tests. Thus the invention also provides a test cell for use in monitoring aggregation of blood platelets in a platelet-containing sample, the test cell comprising a cuvette having mounted in predetermined positions therein a pair of rod-shaped electrodes each of not more than approximately 0.25 mm diameter so that the aggregation can be monitored by monitoring the electrical resistance between the electrodes via the sample.

The present invention is not to be confused with prior proposals for monitoring blood clotting by electrical means. Although the electrical apparatus used for measuring blood clotting is superficially similar, the electrodes are designed with quite different considerations in mind and therefore different in structure as a result. In monitoring blood clotting electrically, it is believed to be the change in ion concentration which brings about a change in resistance which is monitored and for this purpose the surface area of the electrodes should be maximised while in the present invention it should be minimised.

The invention will be further described with reference to the accompanying drawings in which:

FIG. 1 is a very schematic view of a conventional "Born" aggregometer;

FIG. 2 is a typical plot recorded using the apparatus of FIG. 1;

Figure 3:
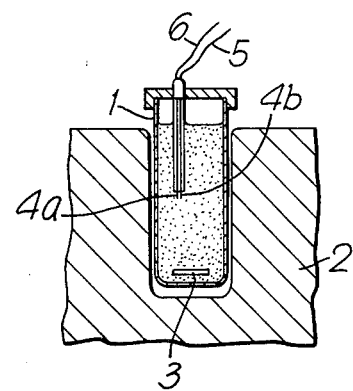
FIG. 3 shows very schematically the test cell of an apparatus according to the present invention.

In FIG. 3 like reference numerals have been used to denote like parts as in the aggregometer of FIG. 1. It will be seen that the principal difference resides in the fact that in place of an optical arrangement for monitoring aggregation, two electrodes 4A and 4B depending from, and mounted on, a lid 5 of the cuvette 1 are used to monitor the platelet aggregation. This is done by means of the circuit shown in FIG. 5 which will be described below and which is connected to the cell by wires 6. The test cell formed by the cuvette, its lid and the electrodes is shown in more detail in FIGS. 6A and 6B and it will be seen that the lid 5 engages with an annular collar 7 supported in turn by an annular shoulder 8 on the cuvette 1. Fixed to and extending through the lid 5 are two tubes 9 and 10. Two 0.25 mm diameter platinum wires are inserted in the tube 9 until about 1.5 cm of the wires project from the lower end of the tube 9. The two wires are insulated from one another down to about 1 cm from their lower ends which are bare and splayed about 1 mm apart. These exposed ends constitute the electrodes 4A, 4B. The tube 10 serves as a guide for a microsyringe by means of which material may be injected in to the liquid sample in cuvette 1.

During monitoring the liquid is stirred by means of a stirring element 3 driven in the conventional manner by magnetic coupling with a rotating drive member (not shown) located outside the cuvette 1 and because of the resulting flow pattern each of the electrodes 4A and 4B should be located off-centre with respect to the cuvette (i.e. displaced from its longitudinal axis) so as to increase the likelihood of platelets adhering to the electrodes.

Figure 5:
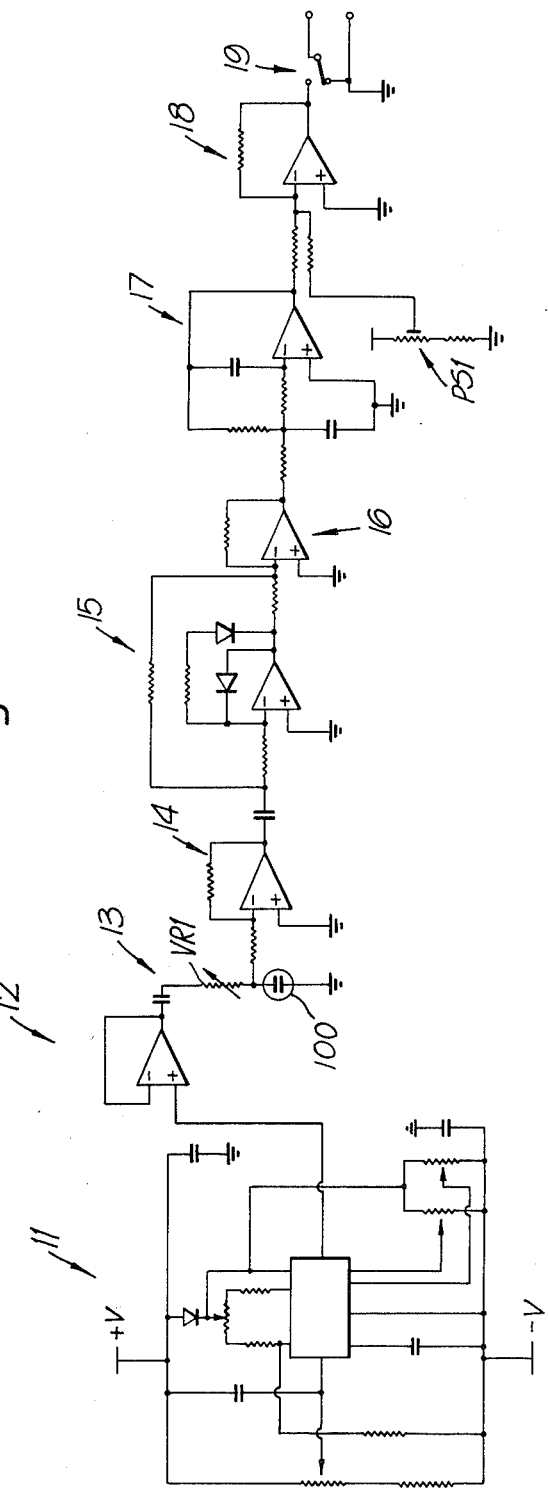
FIG. 5 is a diagram of the circuitry connected to the electrodes in FIG. 3 to form an apparatus according to this invention.
Figure 6A:
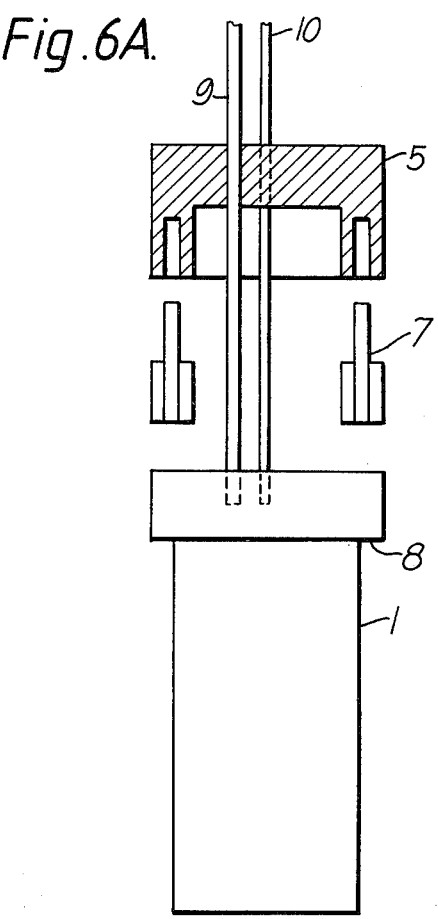
FIG. 6A is a somewhat more detailed sectional view of part of the test "cell" of FIG. 3.
Figure 6B:
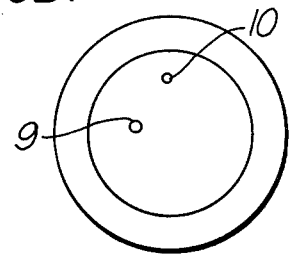
FIG. 6B is a plan view corresponding to FIG. 6A.

The test cell is connected to the circuit shown in FIG. 5 which detects the change in resistance between the electrodes as aggregation proceeds. To this end, it applies a known high frequency AC voltage across a potential divider, one arm of which is formed by the test cell and produces an output e.g. to a moving chart recorder representative of the resistance between the electrodes 4A and 4B. An AC signal is used to avoid polarisation of the electrodes.

The circuit shown in FIG. 5 comprises a reference oscillator 11 based on a type 8038 waveform generator producing a sine wave output of approximately 15 khz which is applied via a buffer 12 and a decoupling capacitor (not referenced) to a potential divider 13, one arm of which is constituted by a 25K variable resistor VR1 and the other arm of which is the test cell. The voltage at the junction of these two elements is amplified by an amplifier 14 and applied to a full-wave rectifier which comprises an operational amplifier in the so-called "perfect rectifier" configuration, that is to say the rectifying diodes are connected in its feed-back loop so that the forward voltage drop across these diodes is eliminated from the output of the rectifier. The output of the rectifier is buffered by an amplifier 16 and applied to a 1 Hz break point low pass filter 17 which produces a DC output voltage with an amplitude proportional to the amplitude of the voltage across the cell 100. This DC voltage is applied together with a voltage from a biasing network, to a zero shifting circuit 18 and a zero correction switch 19 to a chart recorder.

To set up the apparatus, prior to any aggregation of platelets within the sample being caused, the variable resistor VR1 is set to give an output as indicated at the chart recorder corresponding to 100 millivolts across the cell 100. The preset potentiometer PS1 is then set to give zero output on the chart recorder and VR1 can then be used to adjust the output to zero with different samples i.e. blood or plasma.

Figure 4:
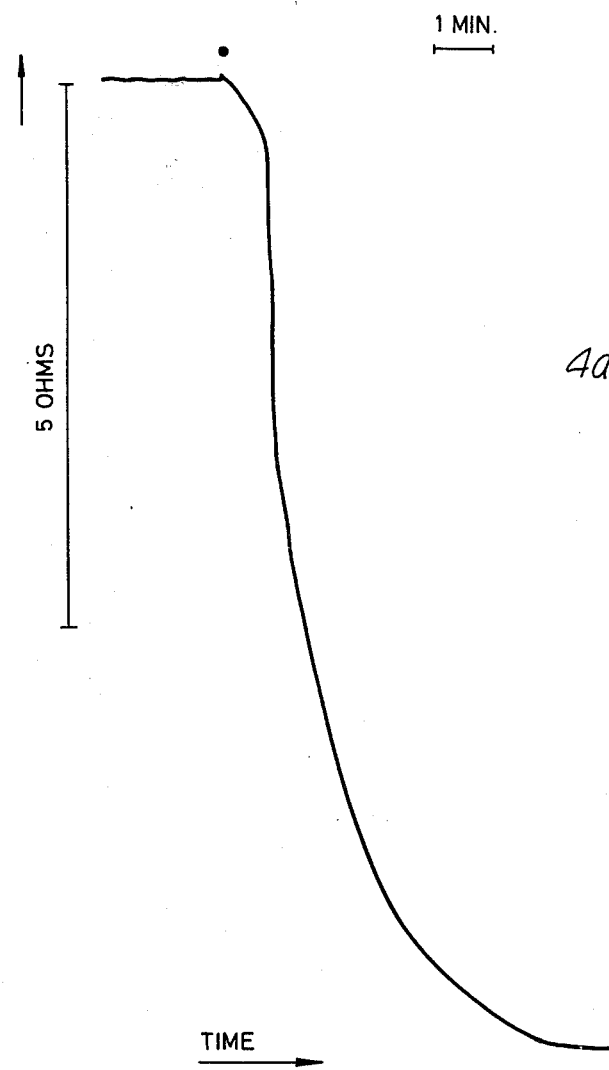
FIG. 4 shows a typical result obtained by use of the apparatus of FIG. 3.

The apparatus is simple and easy to use. A suitable aliquot of PRP or blood (usually 1 ml) is put into a siliconised-glass cuvette 1 which may be of the type ordinarily used with optical aggregometers. The cuvette is warmed to 37° C., the liquid stirred, at constant speed, and the electrode assembly lid 5 is placed in position. When the temperature has stabilized (2–5 min) the apparatus is turned to "record" and the baseline adjusted so that it is exactly "zero" (this guarantees that the correct voltage is applied across the cell) and a few minutes "baseline" recorded. Next the aggregating agent under test is added with a microsyringe through the guide tube 10 in the electrode assembly lid 5. This ensures the agents are delivered to exactly the same spot each time which aids reproducibility. The deflection resulting from the build-up of platelets on the electrodes is conveniently displayed on a conventional laboratory chart recorder. Simultaneous comparisons of aggregation in PRP by the optical and electronic methods indicate that the events recorded by the present apparatus correspond extremely closely to those monitored by the optical machine except that, as comparison of FIGS. 2 and 4 will show, the "noise" in the signal at the beginning and end of aggregation may be less with our apparatus.

Changes in conductance between the electrodes cause a change in the excitation voltage across the cell and this is amplified, rectified and filtered by the circuit of FIG. 5 before being fed via an outlet socket to the chart recorder. After aggregation has occurred the electrode assembly is removed and cleaned with a piece of tissue. The cuvette is rinsed with saline and the apparatus is then ready for another sample.

The efficient operation of the apparatus depends very much upon accurate control of temperature and stirring rate, but it is extremely simple to use and is suitable for measuring the aggregation of platelets within 1–2 mins of obtaining the sample. It is therefore ideal for the assay with labile mediators such as prostacyclin.

As indicated above, a significant aspect of the use of the present apparatus resides in the choice of stirring rate. Reasonably satisfactory results have been obtained with rates of from 400 to 1000 r.p.m. For optimum reproducibility and sensitivity the right combination of stirrer design and r.p.m. is required. The most satisfactory combination tested to date is that of a "Teflon" coated, vaned ferromagnetic bar spun at 600 r.p.m. A suitable commercially available stirrer of this type is the "Spinbar" made by Bell-Art, U.S.A.

In an initial series of experiments, using the present apparatus, we measured the aggregation responses of citrated (or heparinised) human and rabbit PRP by the optical and electronic aggregometers in parallel. Both techniques gave dose related responses to collagen (0.1–10 μg/ml), ADP (1–20 μM), arachidonic acid (1–10 μg/ml, Thrombin (0.1–1.0 U/ml) and prostaglandin endoperoxides (0.05–1.0 μg/ml) and these were antagonised by prostacyclin (1–5 ng/ml) and (in the case of collagen, ADP and arachidonic acid) indomethacin (1–10 μg/ml). Although very similar, there were differences in the results obtained with the two techniques. The present apparatus gave no "shape-change" information, but was on the whole more sensitive, especially to collagen. Biphasic and reversible responses of human blood to ADP (1–4 μM) could be seen with the electronic aggregometer as well as the optical machine although they were not so well marked in the former. In a second series of experiments citrated (or heparinised) rabbit and human Blood was used and the ability of the above agents to induce aggregation was checked. All these stimuli (same concentrations) gave similar dose related responses to those seen in PRP and these could be antagonised by prostacyclin and (in appropriate cases) indomethacin.

Numerous variations in the construction and use of the apparatus are possible. As regards the electrodes, these need not be platinum, and could be of any other suitable material such as for example silver or stainless steel. As mentioned above the test cell and electrodes may be provided as a disposable unit to avoid the need to clean the cell between tests.

One of the electrodes could be coated with collagen—the apparatus could then be used to measure the adhesive property of the platelets.

The construction of the cell may be varied. For example the cell could be arranged so that blood can flow through it during use.

The waveform of the cell excitation voltage may be changed. Any periodic AC waveform may be satisfactory although it should have no net DC level as otherwise undesirable polarisation may result. The 8038 IC is capable of producing, inter alia pulse, sine and triangular waveforms.

We envisage a number of areas of use for our apparatus. Firstly there will be a purely "academic" use. Very many research laboratories have conventional platelet aggregometers for research or teaching purposes and we would anticipate great interest in a machine which performs as well as, (if not better than), the optical machine in PRP, and also works with whole blood. A second important application is in the diagnostic field. Most haematology units in large hospitals have platelet aggregometers of the optical type and we again would anticipate widespread demand for a small robust apparatus able to measure platelet aggregation in blood samples taken at the bedside with no further manipulation of the sample required other than anti-coagulation. Our own experiments have confirmed the feasibility of doing such tests. Amongst the platelet disorders which could be detected using this apparatus include inherited thrombocytopenias or defects such as Von Willebrands disease, the Bernard-Soulier Syndrome, Wiscott-Aldrich Syndrome and May-Hegglin anomaly, Glanzmanns Thrombasthenia and the Portsmouth Syndrome as well as acquired conditions, such as essential thrombocytopenia or uremia.

It is also envisaged that the apparatus may be used to provide a rapid check of the platelet aggregation of the blood of patients about to undergo surgery, etc.

It is also highly likely that in the near future tests will be evolved whereby the sensitivity of platelets to aggregating stimuli will be of value in the diagnosis of many thromboembolic disorders.

We claim:

1. A method of monitoring blood-platelet aggregation in a platelet-containing sample comprising the step of monitoring the change in electrical resistance between rod shaped electrodes immersed in and in contact with the sample while relative movement of the sample and electrodes occurs, the electrodes being not more than approximately 0.25 mm. in diameter.

2. A method according to claim 1 wherein the sample is stirred while said electrical resistance is monitored.

3. Apparatus for monitoring blood-platelet aggregation comprising: a test cell for a platelet-containing sample; a plurality of electrodes and associated means for mounting them in predetermined positions with respect to one another in the test cell so as in use to be immersed in and in contact with such sample, the electrodes each being rod shaped and not more than approximately 0.25 mm in diameter; and circuitry for monitoring the change in electrical resistance between the electrodes.

4. An apparatus according to claim 3 wherein the electrodes are two parallel wires.

5. Apparatus according to claim 3 wherein the test cell comprises a removable lid on which the mounting means is provided.

6. Apparatus according to claim 3 wherein the electrodes are mounted off-centre with respect to said test cell.

7. Apparatus according to claim 3 wherein the electrodes are not more than approximately 2 mm apart.

8. Apparatus according to claim 3 wherein each electrode has approximately 1.5 cm or less of its length exposed to the sample volume.

9. Apparatus according to claim 3 wherein one of the electrodes has a coating comprising collagen.

10. A test cell for use in monitoring aggregation of blood platelets in a platelet-containing sample, the test cell comprising a cuvette having mounted in predetermined positions therein a pair of rod-shaped electrodes each of not more than approximately 0.25 mm diameter so as in use, to be immersed in and in contact with such sample, so that the aggregation can be monitored by monitoring the electrical resistance between the electrodes via the sample.

* * * * *

UNITED STATES PATENT AND TRADEMARK OFFICE
CERTIFICATE OF CORRECTION

PATENT NO. : 4,319,194
DATED : March 9, 1982
INVENTOR(S) : David C. Cardinal et al.

It is certified that error appears in the above-identified patent and that said Letters Patent is hereby corrected as shown below:

On the title page, assignee should read:

-- Burroughs Wellcome Co., Research Triangle Park, N.C. --

Signed and Sealed this

Ninth Day of November 1982

[SEAL]

Attest:

GERALD J. MOSSINGHOFF

Attesting Officer     Commissioner of Patents and Trademarks